US 12,043,826 B2

United States Patent
Chiu

(10) Patent No.: US 12,043,826 B2
(45) Date of Patent: Jul. 23, 2024

(54) SPONTANEOUS NUCLEIC ACID PURIFICATION AND CONCENTRATION IN A SINGLE STEP

(71) Applicant: Phase Scientific International, Ltd., Hong Kong (CN)

(72) Inventor: Yin To Chiu, Hong Kong (CN)

(73) Assignee: PHASE SCIENTIFIC INTERNATIONAL, LTD., Hong Kong (CN)

(*) Notice: Subject to any disclaimer, the term of this patent is extended or adjusted under 35 U.S.C. 154(b) by 966 days.

(21) Appl. No.: 16/961,247

(22) PCT Filed: Jan. 18, 2019

(86) PCT No.: PCT/US2019/014133
§ 371 (c)(1),
(2) Date: Jul. 9, 2020

(87) PCT Pub. No.: WO2019/143895
PCT Pub. Date: Jul. 25, 2019

(65) Prior Publication Data
US 2021/0071165 A1    Mar. 11, 2021

Related U.S. Application Data

(60) Provisional application No. 62/619,285, filed on Jan. 19, 2018.

(51) Int. Cl.
*C12N 15/10* (2006.01)
*C08G 65/331* (2006.01)
*C08G 65/336* (2006.01)

(52) U.S. Cl.
CPC ..... *C12N 15/1006* (2013.01); *C08G 65/3312* (2013.01); *C08G 65/336* (2013.01)

(58) Field of Classification Search
CPC .............. C08G 65/3312; C08G 65/336; C08G 65/3344; C08G 65/337; C12N 15/1006; C07F 7/1804
See application file for complete search history.

(56) References Cited

U.S. PATENT DOCUMENTS

| | | | |
|---|---|---|---|
| 6,132,763 A | 10/2000 | Fisher | |
| 6,399,385 B1 | 6/2002 | Croyle et al. | |
| 7,626,017 B2 | 12/2009 | Laugharn, Jr. et al. | |
| 7,666,583 B2 | 2/2010 | Mor et al. | |
| 7,803,405 B2 | 9/2010 | Keating et al. | |
| 9,823,247 B2 | 11/2017 | Kamei et al. | |
| 10,006,911 B2 | 6/2018 | Kamei et al. | |
| 10,359,423 B2 | 7/2019 | Kamei et al. | |
| 10,578,616 B2 | 3/2020 | Kamei et al. | |
| 11,287,426 B2 | 3/2022 | Kamei et al. | |
| 11,327,075 B2 | 5/2022 | Kamei et al. | |
| 2002/0042506 A1 | 4/2002 | Kristyanne et al. | |
| 2005/0077497 A1 | 4/2005 | Anderson | |
| 2006/0025579 A1 | 2/2006 | Riedl et al. | |
| 2006/0166349 A1 | 7/2006 | Kepka et al. | |
| 2007/0161000 A1 | 7/2007 | Van Alstine et al. | |
| 2008/0242825 A1 | 10/2008 | Devi et al. | |
| 2009/0192111 A1 | 7/2009 | Bader et al. | |
| 2009/0286966 A1 | 11/2009 | Christensen et al. | |
| 2010/0174052 A1 | 7/2010 | Hjorth et al. | |
| 2010/0179252 A1 | 7/2010 | Johansson et al. | |
| 2011/0257378 A1 | 10/2011 | Tran et al. | |
| 2011/0263040 A1 | 10/2011 | Jones | |
| 2013/0164825 A1 | 6/2013 | Gabriele et al. | |
| 2014/0121357 A1 | 5/2014 | Segura Ruiz et al. | |
| 2014/0221549 A1 | 8/2014 | Bodkhe et al. | |
| 2014/0227712 A1 | 8/2014 | Horlitz et al. | |
| 2014/0228549 A1 | 8/2014 | Bernhard et al. | |
| 2015/0166592 A1 | 6/2015 | Guo | |
| 2015/0253320 A1 | 9/2015 | Kamei et al. | |
| 2018/0100854 A1 | 4/2018 | Kamei et al. | |
| 2018/0258419 A1 | 9/2018 | Fischer et al. | |
| 2018/0259521 A1 | 9/2018 | Kamei et al. | |
| 2019/0033308 A1 | 1/2019 | Kamei et al. | |
| 2019/0187140 A1 | 6/2019 | Kamei et al. | |
| 2019/0250156 A1 | 8/2019 | Kamei et al. | |
| 2019/0391143 A1 | 12/2019 | Kamei et al. | |
| 2020/0150116 A1 | 5/2020 | Kamei et al. | |
| 2020/0284791 A1 | 9/2020 | Kamei et al. | |
| 2022/0252598 A1 | 8/2022 | Kamei et al. | |

FOREIGN PATENT DOCUMENTS

| | | |
|---|---|---|
| CN | 101679481 A | 3/2010 |
| CN | 101835790 A | 9/2010 |
| CN | 102264901 A | 11/2011 |

(Continued)

OTHER PUBLICATIONS

Ivanenko et al., Russian Chemical Bulletin, International Edition, 2012, 61(11), pp. 2163-2171. (Year: 2012).*
Khonani et al., Russian Chemical Bulletin, International Edition, 2010, 59(1), pp. 75-80. (Year: 2010).*
Gu et al., Colloids and Surfaces B: Biointerfaces, 2015, 136, p. 1139-1147. (Year: 2015).*
Radi, B., Reinforced hydrogels for silicone copolymer delivery for scar remediation, 2010, PHD thesis, Queensland University of Technology, 255 pages. (Year: 2010).*
Ziegler YS, et al. (2014) Plasma membrane proteomics of human breast cancer cell lines identifies potential targets for breast cancer diagnosis and treatment. PLoS One. 9(7):e102341.
Schindler J, et al. (2008) Aqueous polymer two-phase systems for the proteomic analysis of plasma membranes from minute brain samples. J Proteome Res 7(1):432-442.

(Continued)

*Primary Examiner* — Jonathan S Lau
(74) *Attorney, Agent, or Firm* — EAGLE IP LIMITED

(57) ABSTRACT

The present disclosure relates to a novel material and composition to perform purification and concentration of biological sample or nucleic acid in single step. The present disclosure also relates to a method to use of the same in two phase system to purify and concentrate the target biological materials and/or nucleic acids with an improved detection accuracy for diagnostics performance.

16 Claims, No Drawings

(56) References Cited

FOREIGN PATENT DOCUMENTS

| | | |
|---|---|---|
| CN | 102272144 A | 12/2011 |
| CN | 102421898 A | 4/2012 |
| CN | 103476786 A | 12/2013 |
| CN | 103797023 A | 5/2014 |
| CN | 104707358 A | 6/2015 |
| CN | 106662582 A | 5/2017 |
| CN | 108342383 A | 7/2018 |
| CN | 110003323 A | 7/2019 |
| EP | 0268946 A2 | 6/1988 |
| JP | 2000245460 A | 9/2000 |
| JP | 2002537106 A | 11/2002 |
| JP | 2007525222 A | 9/2007 |
| JP | 2017513015 A | 5/2017 |
| WO | 0050161 A1 | 8/2000 |
| WO | 2002057289 A1 | 7/2002 |
| WO | 2007140417 A2 | 12/2007 |
| WO | 2011159537 A2 | 12/2011 |
| WO | 2014128129 A1 | 8/2014 |
| WO | 2015134938 A1 | 9/2015 |
| WO | 2016155888 A1 | 10/2016 |
| WO | 2017041030 A1 | 3/2017 |
| WO | 2017214315 A1 | 12/2017 |
| WO | 2018039139 A1 | 3/2018 |
| WO | 2018183454 A1 | 10/2018 |
| WO | 2018183465 A1 | 10/2018 |
| WO | 2018222972 A1 | 12/2018 |
| WO | 2019046553 A1 | 3/2019 |
| WO | 2019046563 A1 | 3/2019 |
| WO | 2019055926 A2 | 3/2019 |
| WO | 2019118705 A1 | 6/2019 |
| WO | 2019118712 A1 | 6/2019 |
| WO | 2019143895 A1 | 7/2019 |
| WO | 2019143943 A2 | 7/2019 |
| WO | 2019144016 A1 | 7/2019 |
| WO | 2019144030 A1 | 7/2019 |
| WO | 2021037075 A1 | 3/2021 |
| WO | 2021148393 A1 | 7/2021 |
| WO | 2021185336 A1 | 9/2021 |
| WO | 2022008591 A1 | 1/2022 |

OTHER PUBLICATIONS

Spindler KL, et al. (2015) Circulating free DNA as biomarker and source for mutation detection in metastatic colorectal cancer. PLoS One. 10(4):e0108247.

Riedl W, et al. (2008) Membrane-supported extraction of biomolecules with aqueous two-phase systems[J]. Desalination, 224(1-3): 160-167.

Frerix A, et al. (2005) Scalable recovery of plasmid DNA based on aqueous two-phase separation. Biotechnol Appl Biochem. 42(Pt 1):57-66.

Crucho Cic, et al. (2017) Polymeric nanoparticles: A study on the preparation variables and characterization methods. Mater Sci Eng C Mater Biol Appl. 80:771-784.

Shin H, et al. (2015) High-yield isolation of extracellular vesicles using aqueous two-phase system. Sci Rep. 5:13103.

Zeringer E, et al. (2015) Strategies for isolation of exosomes. Cold Spring Harb Protoc. (4):319-323.

Iqbal M, et al. (2016) Aqueous two-phase system (ATPS): an overview and advances in its applications. Biol Proced Online. 18:18.

Zhou et al. (2015) Nanoparticle Vesicles with Controllable Surface Topographies through Block Copolymer-Mediated Self-Assembly of Silica Nanospheres, Langmuir, vol. 31(48), 11 pp. 13214-13220.

Bashir et al. (2016) Controlled-release of Bacillus thurigiensis formulations encapsulated in light-resistant colloidosomal microcapsules for the management of lepidopteran pests of Brassica crops, PEERJ., vol. 4(e2524). pp. 1-14.

Sigma-Aldrich "Poly(ethylene glycol) octyl ether" Retrieved from the Internet <URL:https://www.google.com/search?q=poly%28ethylene+glycol%29+octyl+ether&source=Int&tbs=cdr%3A1%2Ccd_min%3A%2Ccd_max%3A1%2F18%2F2018&tbm=> <URL https://www.sigmaaldrich.com/catalog/product/sigma/40530?lang=en®ion=US> [retrieved on Jun. 16, 2020].

Wu et al., "Factors Affecting Aqueous Two-Phase Extraction", Biopharmaceutical Technology (Fourth Edition), Aug. 2015, p. 122-126, China medicine science and technology press.

"Silicone Polyethers—Silsurf", Retrieved from the internet <URL: https://www.siltech.com/products/silicone-polyethers-silsurf/#:~: text=Silicone%20polyethers%2C%20or%20silicone%20surfactants,specific%20properties%20of%20a%20product>. [retrieved on Feb. 17, 2023].

Frank Luechau, et al., Partition of plasmid DNA in polymer-salt aqueous two-phase systems, Separation and Purification Technology, Apr. 20, 2009, pp. 397-404, vol. 66, No. 2, Elsevier Science, Amsterdam, NL.

Vijayaragavan K. Saagar et al., Separation of porcine parvovirus from bovine serum albumin using PEG-salt aqueous two-phase system, Journal of Chromatography B, Sep. 1, 2014, pp. 118-126, vol. 967, NL.

Erik Jue et al., Using an aqueous two-phase polymer-salt system to rapidly concentrate viruses for improving the detection limit of the lateral-flow immunoassay: Concentrating Viruses in a Polymer-Salt System, Biotechnology and Bioengineering, Dec. 1, 2014, pp. 2499-2507, vol. 111, No. 12, US.

Paz Sean et al., A simplified SARS-CoV-2 detection protocol for research laboratories, Plos One, Dec. 18, 2020, p. e0244271, vol. 15, No. 12.

Steven B. Zimmerman and Lizabeth D. Murphy, Excluded Volume Effects on the Partition of Single- and Double-Stranded Oligodeoxynucleotides Between Two Liquid Phases, Biopolymers, Oct. 1992, 1365-1373, vol. 32, Issue 10, John Wiley & Sons, Inc.

Steven B. Zimmerman and Stefan O. Trach, Excluded Volume Effects on the Partition of Macromolecules Between Two Liquid Phases, Biopolymers, 1990, 703-718, vol. 30, Issue 7-8, John Wiley & Sons, Inc.

T.Matos, et al., Isolation of PCR DNA fragments using aqueous two-phase systems, Separation and Purification Technology, Feb. 10, 2014, 144-148, vol. 122, Elsevier B.V.

Andreas Frerix, et. al., Exploitation of the Coil-Globule Plasmid DNA Transition Induced by Small Changes in Temperature, pH Salt, and Poly(ethylene glycol) Compositions for Directed Partitioning in Aqueous Two-Phase Systems, Langmuir, Mar. 25, 2006, 4282-4290, vol. 22 Issue 9, American Chemical Society.

Luechau, Frank; et al. (2009) Primary capture of high molecular weight nucleic acids using aqueous two-phase systems. Separation and purification technology, 66.1: 202-207.

Nazer, Behzad; et al. (2017) Plasmid DNA affinity partitioning using polyethylene glycol-sodium sulfate aqueous two-phase systems. Journal of Chromatography B, 1044: 112-119.

Sorber L, et al. (2017) A Comparison of Cell-Free DNA Isolation Kits: Isolation and Quantification of Cell-Free DNA in Plasma. J Mol Diagn. Jan. 19(1):162-168.

Filip Janku; et al., "A novel method for liquid-phase extraction of cell-free DNA for detection of circulating tumor DNA", Scientific reports, 2021, 11(1): 19653.

Ricky Y. T. Chiu, et al., An Aqueous Two-Phase System for the Concentration and Extraction of Proteins from the Interface for Detection Using the Lateral-Flow Immunoassay, PLOS One, Nov. 10, 2015, 1-14, PLOS, California, US.

K. Jessie, et al., Protein Precipitation Method for Salivary Proteins and Rehydration Buffer for Two-Dimensional Electrophoresis, Biotechnology, 2008, 686-693, 7 (4), Asian Network for Scientific Information.

Richard J. Wicks, et al., The extraction and purification of DNA labelled with [methyl-3 H]thymidine in aquatic bacterial production studies, Journal of Plankton Research, 1987, 1159-1166, vol. 9 No. 6, IRL Press Limited, Oxford, England.

Donald C Rio, et al., Purification of RNA by SDS solubilization and phenol extraction, Cold Spring Harb Protoc, Jun. 2010, 1-4, vol. 2010 Issue 6, Cold Spring Harbor Laboratory Press, NY, USA.

(56) References Cited

OTHER PUBLICATIONS

Zsolt CZimmerer, et al., A Versatile Method to Design Stem-Loop Primer-Based Quantitative PCR Assays for Detecting Small Regulatory RNA Molecules, PLOS One, Jan. 31, 2013, 1-10, vol. 8 Issue 1, PLOS, California, US.

Shin Hyunwoo et al., "Aqueous two-phase system to isolate extracellular vesicles from urine for prostate cancer diagnosis", PLOS One, vol. 13, No. 3, Mar. 27, 2018 (Mar. 27, 2018), p. 0194818.

Pereira Matheus M. et al., "Pre-treatment strategies based on aqueous two-phase systems comprising ionic liquids to improve the adrenal cancer diagnosis", Journal of Molecular Liquids, vol. 367, Sep. 22, 2022, p. 120409, XP093103949.

Mendes Maria S. M. et al., "Aqueous two-phase systems as multipurpose tools to improve biomarker analysis", Separation and Purification Technology, vol. 317, Apr. 17, 2023 (Apr. 17, 2023), p. 123875, XP093103947.

Lee, Hoyoon, et al., "Precision cell-free DNA extraction for liquid biopsy by integrated microfluidics." NPJ precision oncology 4.1 (2020): 3.

Ahmed et al., "Aqueous Two-Phase Systems and Microfluidics for Microscale Assays and Analytical Measurements", Annual Review of Analytical Chemistry, 2021 14:1, 231-255.

Fei Yu, et al., "Comparative Evaluation of Three Preprocessing Methods for Extraction and Detection of Influenza A Virus Nucleic Acids from Sputum", Front Med (Lausanne), 2018 year, vol. 5:56.

Piotr Chomczynski, et al., "The single-step method of RNA isolation by acid guanidinium thiocyanate-phenol-chloroform extraction: twenty-something years on", Nature Protocols, 2006, 1(2), 581-585.

\* cited by examiner

SPONTANEOUS NUCLEIC ACID PURIFICATION AND CONCENTRATION IN A SINGLE STEP

CROSS-REFERENCE TO RELATED APPLICATIONS

This application claims the benefit of U.S. Provisional Application No. 62/619,285, filed Jan. 19, 2018. The entire contents and disclosures of the preceding application are incorporated by reference into this application.

Throughout this application, various publications are cited. The disclosures of these publications in their entireties are hereby incorporated by reference into this application to more fully describe the state of the art to which this invention pertains.

FIELD OF THE INVENTION

The present disclosure relates to a novel material and composition to perform purification and concentration of a biological sample or nucleic acid in a single step. Also disclosed is a method of using salts and a polymer-modifier complex in a two phase system (alternatively, "aqueous two phase system") to purify and concentrate a target biological material and/or nucleic acid.

BACKGROUND OF THE INVENTION

New biomarkers and medicines for many diseases are discovered or invented in recent years. Numerous patients still die from these diseases every year. The patients die because health care professionals cannot detect the diseases at an early stage or do not detect the diseases at all. Many of these diseases do not show any symptoms at early stages. By the time symptoms develop, the patients are already at late or end stages. There is not much a health care professional can do to treat the patients or to save their lives. If these diseases are diagnosed early, these patients are likely to be cured fully by applying the right procedures or using suitable medicines. While examining the patients, experienced health care professionals may suspect that the patients have certain diseases. However, the concentration of the biomarkers in the patients at early stage is usually so insignificant to be detected. Health care professionals cannot prescribe suitable medicines if the diagnostic technique cannot confirm the contraction of a disease. The predicament is that biomarkers of a disease exist in a patient but they are unable to be detected. Existing medicines may cure the disease but they are not prescribed. All these issues are the result of not detecting the disease early.

It has been a huge challenge to detect the existence of an analyte which has an extremely minute concentration. The analyte can be a biomarker of a disease such as a cell free DNA (cfDNA), circulating tumor DNA (ctDNA) or a protein which may exist in a sample of patient saliva, blood, urine or other body fluid. Many of the existing diagnostic or detection methods may falsely report that the analyte does not exist if the concentration is too low. The gold standard of diagnostics such as Polymerase Chain Reaction (PCR) and Enzyme-Linked Immunosorbent Assay (ELISA) may produce a false negative result if the targeted analyte has extremely low concentration.

For example, cfDNA extracted from liquid biopsies has become an attractive biomarker for several pathologic conditions. For example, ctDNA likely released from apoptotic or necrotic tumor cells can be used to monitor cancer progression and relapse throughout treatment with potentially greater sensitivity than current gold standard imaging methods like CT, PET, and MRI. In comparison to a tumor biopsy that is taken from a region of the solid tumor, liquid biopsies are noninvasive, can be collected at multiple time points, and can yield ctDNA that better represents the diversity of the tumor, which is useful for identifying drug-resistant mutations.

Additionally, cfDNA of the fetus can indicate various abnormalities during pregnancy such as aneuploidies, which can be done earlier than current prenatal testing methods like chorionic villi sample and amniocentesis, without the risk of spontaneous abortion. Liquid biopsies of heart transplant patients can reveal donor cfDNA, which can be a warning sign that the patient will reject the transplant in the upcoming weeks or months.

Despite new biomarkers and medicines for many diseases are discovered or invented in recent years, these new biomarkers, such as cfDNA testing, have not been adopted in routine clinical procedures due to lack of sensitivity and specificity. Because they are present in low quantities, detection hinges upon isolation methods that can concentrate the biomarkers from background. Depending on the isolation method, this challenge can be complicated with variance in fragment size and influences by test inhibitors.

There are purification products widely used in literature to concentrate cfDNA. However, these expensive product kits are limited by the maximum sample volume they can process, as well as the amount of DNA that can be purified before clogging. In addition, those procedure are always time consuming, tedious, costly and involve the use of hazardous organic solvents.

Conventionally, the purification and concentration process for a biological sample or nucleic acid usually requires multiple step operations such as a series of centrifugation, precipitation and/or incubation. The conventional method is complex, unreliable and inefficient, and the purity and yield of the product is not good. Therefore, a novel, simplified and single step purification and concentration process for biological samples or nucleic acids is highly demanded in the commercial industry, where the method should be accurate, inexpensive, simple and easy to handle, safe, user friendly and fast.

To overcome these limitations, this invention uses novel methods and devices to obtain a biological sample or nucleic acid for further analysis easily and quickly in a single step using an improved two phase system without the need of complex equipment. The methods and devices can perform the following multiple tasks, including but not limited to cell lysis, removing non-targeted biomolecules and/or concentrating targeted biomolecules. Concentrating biomolecules or removing inhibitors will improve detection accuracy and diagnostic performance. What could not be detected before will become possible. Many life-threatening diseases are cured if the diseases are detected early.

SUMMARY OF THE INVENTION

The present invention provides a novel material for spontaneous target biological sample or nucleic acid purification and concentration in a single step. The novel material comprises a polymer and modifying agent (modifier).

More particularly, the present invention provides a novel material for spontaneous target biological sample or nucleic acid purification and concentration in a single step using a two phase system. The novel material comprises a polymer and modifying agent (modifier).

In a preferred embodiment, the present invention provides a novel material for spontaneous target biological sample or nucleic acid purification and concentration in a single step using a two phase system. The novel material comprises a polymer and modifying agent (modifier). Some covalent and/or non-covalent bonds form between the modifying agent and polymer.

In particular, the binding affinity of target biological sample or nucleic acid on the novel material is significantly and unexpectedly enhanced due to the networking of the polymer-modifier complex. In one embodiment, the binding affinity of target biological sample or nucleic acid for the polymer phase comprising the polymer-modifier complex is significantly enhanced. In one embodiment, ~90%-100% target biological samples or nucleic acids are bound to the polymer-modifier complex.

The present invention provides a novel composition for spontaneous target biological sample or nucleic acid purification and concentration in a single step. The novel composition comprises a polymer and modifying agent (modifier).

In particular, the present invention provides a novel composition for spontaneous target biological sample or nucleic acid purification and concentration in a single step using a two phase system. The novel composition comprises a polymer and modifying agent (modifier).

In one particular embodiment, the present invention provides a novel composition for spontaneous target biological sample or nucleic acid purification and concentration in a single step using a two phase system. The novel composition comprises a polymer and modifying agent (modifier) which together form a novel polymer-modifier complex with some covalent/non-covalent bonds.

Even more particularly, the binding affinity of target biological sample or nucleic acid on the novel composition comprising a polymer and modifying agent (modifier) is significantly and unexpectedly enhanced due to the networking of the polymer-modifier complex.

The present invention provides a novel method for spontaneous target biological sample or nucleic acid purification and concentration in a single step. The novel composition comprises a polymer and modifying agent (modifier).

In particular, the present invention provides a novel method for spontaneous target biological sample or nucleic acid purification and concentration in a single step using a two phase system. The novel composition comprises a polymer and modifying agent (modifier).

In one particular embodiment, the present invention provides a novel method for spontaneous target biological sample or nucleic acid purification and concentration in a single step using a two phase system. The novel method makes use of a polymer and modifying agent (modifier) to form a novel polymer-modifier complex with some covalent/non-covalent bonds.

In particular, the target biological samples or nucleic acids will be bound only to the polymer-modifier complex, while the unwanted materials will stay in the salt phase and be easily removed.

The present methods involve the use of polyethylene glycol (PEG) and a modifying agent, such as urea or organosilicon. Some covalent and/or non-covalent bonds can form between PEG and urea or organosilicon.

In particular, the present invention provides a method to perform purification and concentration of a biological sample or nucleic acid in a single step using a two phase system. The two phase system includes one phase of salts and one phase of a polymer-modifier complex.

The present invention provides a method to simplify the purification and concentration process of a biological sample or nucleic acids from various sources by minimizing the steps in a cycle purification process. In the present method, the use of organic solvents including alcohol for lysis, extraction or washes is eliminated. The present method produces biological samples or nucleic acids in purity and concentration that are suitable for further characterization and downstream processing. The downstream applications of purified biomolecules may include analyte detection, sensing, forensic, diagnostic or therapeutic applications, sequencing, amplification, PCR, sequencing or blotting procedures, and the like. Because of the unique features described herein, the present method is readily adaptable to automation including high throughput screening systems.

DETAILED DESCRIPTION OF THE INVENTION

Here, unless indicated otherwise, the terms used in the specification including technical and scientific terms have the same meaning as those that are usually understood by those skilled in the art to which the present invention pertains, and detailed description of the known functions and constitutions that may obscure the gist of the present invention will be omitted.

In this invention, the nucleic acids can be DNA, such as genomic DNA. The nucleic acids may also be RNA, such as total RNA. The nucleic acids can be single-stranded or double-stranded nucleic acid, such as short double-stranded DNA fragments.

The nucleic acid-containing material can be selected from the group consisting of blood, plasma, serum, tissues, bacteria, viruses, RNA viruses, smear preparations, bacteria cultures, cell cultures, urine, cell suspensions and adherent cells, polymerase chain reaction (PCR) reaction mixtures and in vitro nucleic acid modification reaction mixtures. The nucleic acid-containing material may comprise human, animal or plant material. The method according to the invention may also include the use of plasmid DNA from *Escherichia coli* for subsequent cloning or sequencing for molecular biology analysis. Nucleic acids also include oligonucleotides within the meaning of the method according to the invention. Furthermore, the nucleic acids may be derived from sequencing reactions or other comparable reactions. The nucleic acid-containing material can be from biological fluids such as human blood and serum, cultured cells, tissues from plants, animal and human, and other specimens. The nucleic acids, especially DNA, in blood samples are used for the purposes of diagnosis of genetic disease, diagnosis and monitoring of blood borne parasitic disease such as malaria, the determination of paternity, and the monitoring of other unusual cell populations in the blood as can occur in some neoplasia.

The method described herein is also useful for the isolation of both double stranded (ds) and single stranded (ss) polynucleotides (e.g., DNA, RNA, PNA) of virtually any size and from a wide variety of sources. In this invention, the novel method can isolate a wide range of nucleic acids. In the invention, only certain DNA, RNA, and/or PNA with a desired size range can be subsequently collected and concentrated. The desired fragments are less than or equal to 100 bp or mers, less than or equal to 200 bp or mers, less than or equal to 300 bp or mers.

The present invention provides a method for spontaneous purification and concentration of target biological samples or nucleic acids in a single step using a two phase system.

The two phase system, after phase separation, includes a salt phase (alternatively "salt-rich phase") containing salt and a polymer phase (alternatively, "polymer-rich phase" or "polymer complex-rich phase") containing the polymer-modifier complex. The salt phase or salt-rich phase refers to the phase in which the salt is predominantly distributed after phase separation. The polymer phase, polymer-rich phase or "polymer complex-rich phase" refers to the phase in which the polymer or polymer-modifier complex is predominantly distributed after phase separation.

In the present invention, the salts are selected from organic and inorganic salts, including but not limited to potassium phosphate, sodium sulfate, magnesium sulfate, ammonium sulfate, sodium citrate, sodium chloride, sodium acetate, ammonium chloride, potassium citrate, sodium phosphate, calcium phosphate, ammonium phosphate, ammonium acetate, magnesium phosphate, potassium sulfate, magnesium sulfate, and calcium sulfate. In one embodiment, cations for the salt include, but are not limited to, straight or branched trimethyl ammonium, triethyl ammonium, tripropyl ammonium, tributyl ammonium, tetramethyl ammonium, tetraethyl ammonium, tetrapropyl ammonium and tetrabutyl ammonium. In one embodiment, cations for the salt include, but are not limited to, phosphate, sulphate, nitrate, chloride and hydrogen carbonate. In one embodiment, any combinations of the above salts are used.

In the present invention, the polymer can be selected from polyethylene glycol (PEG), polypropylene glycol, polyvinyl alcohol, polyvinyl pyrrolidone, methyl cellulose, ethylhydroxyethyl cellulose, propylene glycol, methoxypolyethylene glycol, Dextran, Ficoll, polyvinyl pyrrolidone, polyvinyl alcohol, hydroxypropyl starch, hydroxypropyl dextran, maltodextrin, and dextran. In one embodiment, the preferred polymers are dextran, polyethylene glycol (PEG), and polypropylene glycol.

In the present invention, any suitable PEG can be used in the compositions and methods of the invention. It can be, for example, PEG 1000 or PEG 2000 or PEG 4000 or PEG 8000 or PEG 10000 or PEG 12000.

In the present invention, the modifying agents are chemicals that can form some covalent and/or non-covalent bonds with the polymer. The modifying agents can be, for example, urea, organosilicon, polyacetylene carbamide derivatives, polyols, or polyacids.

In one embodiment, the functional groups in the organosilicon are selected from the group consisting of hydroxyl, carbonyl, carboxyl, amide, primary and secondary amines. In one embodiment, the organosilicon is

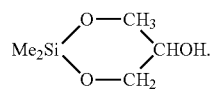

In another embodiment, the organosilicon is

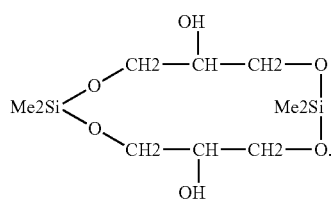

In another embodiment, the organosilicon is $[(CH_3)_2SiCH_2CH_2CONHCH_2CH_2Si(CH_3)_2O]_n$ wherein n has a value of at least 2 (U.S. Pat. No. 2,607,793).

In one embodiment, the polyols include, but are not limited to, erythritol, xylitol and sorbitol. In one embodiment, the polyacids include, but are not limited to, carboxymethylcellulose, carboxymethylstarch, alginic acid, polyacrylate, polymethacrylate, poly(sulfopropyl acrylate), poly(2-acrylamido 2-methyll-propane sulfonic acid) and their salts.

In one embodiment, both the amide and carbonyl functional groups on the organosilicon can interact non-covalently with the hydroxyl functional group on PEG and form a polymer network together with other non-covalent bonds such as hydrogen bonding. In one embodiment, the hydrogen bonding can be —OH . . . O< between polymer and modifiers, among different polymer chains, or within same polymer chain. As a result, a polymer network will be formed. In one embodiment, a polymer network is formed by covalent bonding with or without non-covalent bonding. The polymer network was found to be more effective in capturing/holding the biological materials or nucleic acids, in comparison to that without network. As a result, in some embodiments, target analyte can be concentrated up to 10×, 100×, or even more.

In one embodiment, both the oxygen functional groups on the organosilicon can interact with the hydroxyl groups on PEG to form a polymer network and other non-covalent bonds such as hydrogen bonds. In one embodiment, the hydrogen bonds can be —OH . . . O═, or —OH . . . O< between polymer and modifier, among different polymer chains, or within same polymer chain. As a result, a polymer network will be formed. In one embodiment, a polymer network is formed by covalent bonds with or without non-covalent bonds. The polymer network is found to be more effective in capturing/holding the biological material or nucleic acid. As a result, in some embodiments, target analyte can be concentrated up to 10×, 100×, or even more.

In the present invention, a polymer-modifier complex can be prepared by the following procedure:
  (1) providing an aqueous phase comprising a modifier;
  (2) providing an organic phase comprising a polymer;
  (3) dispersing the organic phase into the aqueous phase; and
  (4) allowing the modifier and polymer to react at the interface of the organic phase and aqueous phase to form the polymer-modifier complex via covalent and/or non-covalent bonds; and
  (5) isolating said polymer-modifier complex.

In one embodiment, the polymer-modifier complex is a PEG-organosilicon complex which can be prepared by the following procedure:
  (1) providing an aqueous phase comprising an organosilicon;
  (2) providing an organic phase comprising PEG;
  (3) dispersing the organic phase into the aqueous phase;
  (4) allowing the PEG and organosilicon to react at the interface of the organic phase and aqueous phase to form said PEG-organosilicon complex; and
  (5) isolating the PEG-organosilicon complex.

In one embodiment, the polymer-modifier complex is isolated as a solid or a suspension. In one embodiment, the polymer-modifier complex in solid is re-dispersed into a water or buffer. In one embodiment, the suspension of polymer-modifier complex obtained or isolated is used for binding a target biological sample or nucleic acid. In one embodiment, the suspension of polymer-modifier complex as obtained from the reaction is directly used for subsequent binding, isolation and/or purification of analyte. In one embodiment, the obtained suspension of polymer-modifier complex first undergoes a simple purification, such as membrane filtration, to lead to a suspension substantially free of reactants and other impurities with a low molecular weight. In one embodiment, the suspension of polymer-modifier complex has an average particle size with a range from 10 nm to 500 nm. In one embodiment, the suspension also undergoes a further purification such as centrifugation to obtain a suspension with an average particle size within a specific range such as 10 nm to 100 nm.

It was surprisingly found that the present polymer-modifier complex can significantly enhance the quantity of nucleic acids collected. The binding affinity of target biological sample or nucleic acids on the polymer-modifier complex is significantly enhanced due to the networking of the polymer-modifier complex. In one embodiment, the binding affinity of target biological samples or nucleic acids for the polymer phase comprising the polymer-modifier complex is significantly enhanced. In one embodiment, about 90%-100% target biological samples or nucleic acids are bound to the polymer-modifier complex. The polymer-modifier complex is found to be more effective in binding the target biological samples or nucleic acids. As a result, the target biological samples or nucleic acids will be found predominantly in the phase containing the polymer-modifier complex and concentrated up to 10×, 100×, or even more.

In one embodiment, the amount of modifier is less than 20% of the total weight of the polymer. In one embodiment, the amount of modifier is ~10%, ~5% ~ or 3% of the total weight of the polymer.

In one embodiment, the polymer-modifier complex can be suspended in water or other aqueous system. In one embodiment, the particle of the polymer-modifier complex in the suspension or solution has an average particle diameter of 100 nm to 1 micron meter. In one embodiment, the particle of the polymer-modifier complex in the suspension or solution has an average particle diameter of 10 to 500 nm. In one embodiment, the particle of the polymer-modifier complex in the suspension or solution has an average particle diameter of 100 to 250 nm. In one embodiment, the particle of the polymer-modifier complex in the suspension or solution has an average particle diameter of 10-250 nm. In one embodiment, the particle of the polymer-modifier complex in the suspension or solution has an average particle diameter of 20-100 nm. In one embodiment, the particle of the polymer-modifier complex in the suspension or solution has an average particle diameter of 10-75 nm. In one embodiment, the particle of the polymer-modifier complex in the suspension or solution has an average particle diameter of 20-50 nm.

In this invention, it is found that the concentrations of salt and polymer-modifier complex can be adjusted to control the affinity of a target analyte to the polymer-modifier complex and the distributions in each phase. It is because said concentrations can affect the binding abilities of biological sample and/or nucleic acids.

In one embodiment, the concentration of polymer-modifier complex is 5-40% (w/w). In one embodiment, the concentration of polymer-modifier complex is 5-30% (w/w). In one embodiment, the concentration of polymer-modifier complex is about 20% (w/w) up to the limit of the complex's solubility. In one embodiment, the concentration of salt is 4-30% (w/w). In one embodiment, the concentration of salt is 3-20% (w/w). In one embodiment, the concentration of salt employed is about 11% (w/w) up to the limit of the salt's solubility.

In one embodiment of the present invention, a salt and the polymer-modifier complex applied to the two phase system can control the affinity of target biological materials (or substances) or nucleic acids described herein for the two phases. In one embodiment, the process for purifying and/or concentrating target biological materials and/or nucleic acids comprises the steps of:
 (1) Preparing the target biological materials or nucleic acids in a buffer solution to form a target buffer solution;
 (2) Adding salt and polymer-modifier complex to the target buffer solution, to form a mixture;
 (3) Allowing the mixture to separate into a polymer phase and a salt phase;
 (4) Optionally discarding the salt phase; and
 (5) Extracting the polymer phase containing the target biological materials or nucleic acids bound to the polymer-modifier complex.

In one embodiment, the process comprises the steps of:
 (1) Preparing target biological materials or nucleic acids in a buffer solution to form a target buffer solution;
 (2) Adding salt and polymer-modifier complex to the target buffer solution to form a first mixture;
 (3) Allowing the first mixture to separate into a first polymer phase and a first salt phase; (4) Detecting the concentration or quantity of the target biological materials or nucleic acids in the first polymer phase;
 (5) If said concentration and/or quantity of said target biological materials or nucleic acids in said first polymer phase is insufficient for subsequent analysis, mixing the first polymer phase with a new salt solution to form a second mixture, allowing said second mixture to separate into a second polymer phase and a second salt phase;
 (6) Repeating steps 4-5 as many times until a sufficient concentration or quantity of said target biological materials or nucleic acids in a final polymer phase is obtained; and
 (7) Extracting the final polymer phase in step (6) from the corresponding final salt phase, thereby obtaining a purified and/or concentrated target biological materials or nucleic acids.

In one embodiment, the process further comprises a step of isolating the purified and/or concentrated biological materials/substances or nucleic acids from the polymer-modifier complex.

In one embodiment, the subsequent analysis includes but is not limited to various downstream applications including analyte detection, sensing, forensic, diagnostic or therapeutic applications, sequencing, amplification, and the like. In one embodiment, the subsequent analysis also includes later nucleic acid based biochemical and diagnostic detection procedures, such as large scale genomic mapping, post DNA shearing, library construction, and for next generation sequencing platform. In one embodiment, the concentration and/or quantity of analyte required for the analysis varies depending on the corresponding method and device.

In the present invention, suitable buffers for biological sample or nucleic acid-containing materials are Tris-EDTA (TE) buffers comprising tris(hydroxymethyl) aminomethane (Tris), ethylenediaminetetraacetic acid (EDTA) and polyadenylic acid. The concentration can be 10 mM Tris (pH 8.0), 50 µM EDTA, and 20 µg/mL polyadenylic acid.

In the present invention, there is provided an aqueous two phase system which comprises an aqueous two phase system and a solid matrix. In one embodiment, the solid matrix is a porous solid matrix.

In the present invention, a suitable two-phase system after phase separation comprises a polymer-rich phase containing at least one water dispersible polymer and a salt-rich phase containing at least one water soluble inorganic or organic salt, wherein said water dispersible polymer is a polymer-modifier complex. In one embodiment, said complex is PEG-urea or PEG-organosilicon. In one embodiment, said salt is potassium phosphate.

In the present invention, the two phase system can be embedded in a solid matrix. The solid matrix can be, but are not limited to, any types of paper, polymer foams, cellulose foams, foams, rayon fabric, cotton fabric, fabric, wood, stones and carbon fibers. Fiber-glass paper, cotton-based paper, single-layer matrix paper and polyolefin foam pad are preferred in the invention.

In the present invention, the purified and concentrated target biological material or nucleic acid can be collected from a polymer-modifier complex. The concentration factors achieved can be up to 10×, 100×, or even more in some embodiments.

In one embodiment, the immobilized nucleic acid on polymer-modifier complex-modified porous paper is eluted out of the porous paper using appropriate elution buffers or deionized water. In one embodiment, the isolated phase containing nucleic acids is not eluted but is stored on the porous paper for future use. For instance, after the isolation of nucleic acids using the present invention, the porous paper containing the target nucleic acids is dried and stored. In one embodiment, nucleic acids retained on the porous paper can be directly eluted for further analysis or treatment. In one embodiment, nucleic acids retained on the porous paper can be first dried and subsequently eluted for further analysis or treatment. The selection of the elution buffer may depend on the contemplated use of the purified nucleic acids. Examples of suitable elution buffers includes, but are not limited to, Tris-EDTA (TE) buffer, aqua bidest and PCR buffer. In one embodiment, the purified nucleic acid on porous paper is eluted in a tube containing TE buffer (10 mM Tris·Cl, 1 mM EDTA solution with pH 7.5), and the purified nucleic acids are recovered in a relatively small volume, e.g., less than 100 µL, and can be used for various downstream applications including analyte detection, sensing, forensic, diagnostic or therapeutic applications, sequencing, amplification, and the like. It can be used in later nucleic acid based biochemical and diagnostic detection procedures, such as large scale genomic mapping, post DNA shearing, library construction, and for next generation sequencing platform.

In one embodiment, the purified nucleic acid on polymer-modifier complex-modified porous paper can be eluted for further analysis, including PCR, RT-PCR, real-time PCR, and real-time RT-PCR. The nucleic acids are eluted by means of an aqueous buffer. The selection of the buffer is determined by the contemplated use of the purified nucleic acid. Examples of suitable buffer are TE buffer, aqua bidest and PCR buffer. In one embodiment, TE buffer is used, and the purified nucleic acid on porous paper is eluted in a tube containing TE buffer (10 mM Tris·Cl, 1 mM EDTA solution at pH 7.5), and the purified nucleic acids are recovered in a relatively small volume, e.g., less than 100 µL.

In one embodiment, the present invention can be integrated with additional diagnostic assay such as Lateral Flow Assay (LFA). The seamless transition between concentration and detection will allow a patient or end user to get test result in a simple single step.

In one embodiment, the present invention can be integrated with enzyme-linked immunosorbent assay (ELISA) and specific antibody-antigen. There are two huge benefits. Firstly, the lengthy time spent on assessing conjugated enzyme activity via incubation with a substrate to produce a measurable product will be cut short. The present sample preparation method functions isothermally and based only on thermal dynamic principles. In various embodiments, the whole sample preparation process will take only 10 minutes to about an hour instead of hours or even days. Secondly, the otherwise low concentration of targeted biomolecules such as peptides, proteins, antibodies and hormones can be increased significantly by the present sample preparation method. The concentration can be improved by 10 folds to even 100 folds in some embodiments.

In one embodiment, the present invention can be integrated with polymerase chain reaction (PCR). Very minute concentration of DNA ladder is concentrated to much higher level. Originally minute concentration of DNA may not be detected and processed by existing sample preparation kits in the art which have strong requirements and limitations on sample volume sizes. After being processed by the present sample preparation method, the targeted DNA concentration may be improved 10 folds to 1000 folds. Thus, the required sample volume size is substantially reduced and the amplification and sensitivity of PCR test can be much improved.

In one embodiment of the present invention, a method is provided for a rapid purification and concentration of biological material and nucleic acid using a two phase system comprising a water soluble salt and a water dispersible polymer, such as polymer modifier complex, by isolating the target biological material or nucleic acid from a small amount of sample without using special equipment. It is more rapid and convenient, and simpler than existing methods in the art intended for the same purposes.

In one embodiment, the present invention provides a polymer-modifier complex prepared by the steps of:
(a) dispersing an organic phase comprising a modifier into an aqueous phase comprising a polymer;
(b) allowing the polymer and modifier to react at the interface of the organic phase and aqueous phase to form the polymer-modifier complex, wherein a polymer network is formed by covalent and/or non-covalent bonds within the polymer-modifier complex, and
(c) isolating the polymer-modifier complex in a form of suspension or solid.

In one embodiment, the polymer includes but is not limited to polyethylene glycol (PEG), activated PEG, polypropylene glycol, polyvinyl alcohol, polyvinyl pyrrolidone, methyl cellulose, ethylhydroxyethyl cellulose, propylene glycol, methoxypolyethylene glycol Dextran, Ficoll, polyvinyl pyrrolidone, polyvinyl alcohol, hydroxypropyl starch, hydroxypropyl dextran, maltodextrin, and dextran.

In one embodiment, the modifier includes but is not limited to ureas, organosilicons, polyacetylene carbamide derivatives, polyols and polyacids.

In one embodiment, the PEG includes but is not limited to PEG 1000, PEG 2000, PEG 4000, PEG 8000, PEG 10000 and PEG 12000.

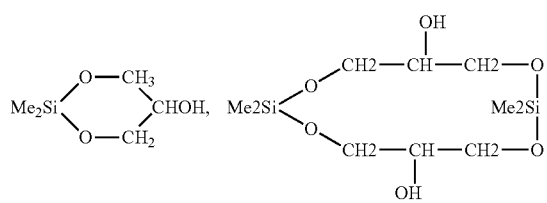

In one embodiment, the organosilicons include but are not limited to and $[(CH_3)_2SiCH_2CH_2CONHCH_2CH_2Si(CH_3)_2O]_n$ wherein n has a value of at least 2.

In one embodiment, the polyols include but are not limited to erythritol, xylitol and sorbitol.

In one embodiment, the weight ratio of the modifier to the polymer is in a range of 3% to 20%.

In one embodiment, the polymer-modifier complex is suspended in water or buffer with an average particle diameter in a range of 10 nm to 500 nm. In one embodiment, the polymer-modifier complex is suspended in water or buffer with an average particle diameter in a range of 20 nm to 250 nm.

In one embodiment, the present invention provides a method of purifying and/or concentrating biological substances or nucleic acids using the polymer-modifier complex as described herein. In one embodiment, the method comprises the steps of:

(1) preparing a buffer solution containing the biological substances or nucleic acids;
(2) adding a salt and the polymer-modifier complex to the buffer solution, resulting a mixture; and
(3) allowing the mixture to separate into a polymer phase and a salt phase, wherein said biological substances or nucleic acids are purified and/or concentrated predominantly partition in said polymer phase containing said polymer-modifier complex.

In one embodiment, the method further comprises a step of separating the biological substances or nucleic acids from the polymer-modifier complex.

In one embodiment, the polymer network formed within the polymer-modifier complex significantly enhances the binding affinity of the biological substances or nucleic acids for the polymer phase.

In one embodiment, 90-100% of the biological substances or nucleic acids are bound to the polymer-modifier complex.

In one embodiment, the concentration of the purified or concentrated biological substances or nucleic acids is 10-100 times higher than that of the biological substances or nucleic acids in the buffer solution in step (1).

In one embodiment, the buffer solution is a Tris-EDTA (TE) buffer.

In one embodiment, the salt includes but is not limited to potassium phosphate, sodium sulfate, magnesium sulfate, ammonium sulfate, sodium citrate, sodium chloride, sodium acetate, ammonium chloride, ammonium acetate, potassium citrate, sodium phosphate, calcium phosphate, ammonium phosphate, magnesium phosphate, potassium sulfate, magnesium citrate, calcium sulfate and any combination thereof.

In one embodiment, the cations of the salt include but are not limited to trimethyl ammonium, triethyl ammonium, tripropyl ammonium, tributyl ammonium, tetramethyl ammonium, tetraethyl ammonium, tetrapropyl ammonium and tetrabutyl ammonium.

In one embodiment, the anions of the salt include but are not limited to phosphates, sulfates, nitrate, chloride, citrates, acetate, and carbonates.

In one embodiment, the mixture comprises 5-40% (w/w) of the polymer-modifier complex.

In one embodiment, the mixture comprises 4-30% (w/w) of the salt.

In one embodiment, the present invention provides a method of purifying and/or concentrating target biological materials/substances or nucleic acids using the polymer-modifier complex as described herein. In one embodiment, the method comprises the steps of:

(1) preparing the target biological materials/substances or nucleic acids in a buffer solution to form a target buffer solution;
(2) adding salt and polymer-modifier complex to the target buffer solution to form a first mixture;
(3) allowing the first mixture to separate into a first polymer phase and a first salt phase, wherein the target biological materials/substances or nucleic acids predominantly partition in the first polymer phase;
(4) detecting the concentration and/or quantity of the target biological materials/substances or nucleic acids in the first polymer phase,
(5) if the concentration or quantity of the target analyte from step (4) is insufficient for a subsequent analysis, mixing the first polymer phase with a new salt solution to form a second mixture, allowing the second mixture to separate into a second polymer phase and a second salt phase;
(6) repeating steps 4-5 as many times until a sufficient concentration or quantity of the target biological materials/substances or nucleic acids in a final polymer phase is obtained; and
(7) isolating the final polymer phase in step (6) from the corresponding final salt phase, thereby obtaining a purified and/or concentrated the target biological materials/substances or nucleic acids.

Throughout this application, it is to be noted that the transitional term "comprising", which is synonymous with "including", "containing" or "characterized by", is inclusive or open-ended, and does not exclude additional, un-recited elements or method steps.

EXAMPLES

The present invention will be described in more detail with reference to the following examples. However, the following examples are provided only for assisting in the entire understanding of the present invention, and do not intend to limit the scope of the present invention. One skilled in the art will readily appreciate that the examples provided are merely for illustrative purposes and are not meant to limit the scope of the invention which is defined by the claims following thereafter.

Here, unless indicated otherwise, the terms used in the specification including technical and scientific terms have the same meaning as those that are usually understood by those who skilled in the art to which the present invention pertains, and detailed description of the known functions and constitutions that may obscure the gist of the present invention will be omitted.

Example 1: Preparation of PEG-Organosilicon Complex a) Drying PEG 8000

PEG 8000 (sigma) was dissolved in benzene (B.P. 79°-80° C.) and the water-organic azeotrope (B.P. 65° C.) was distilled off. PEG 8000 was recovered by removal of solvent under reduced pressure, and was finally dried overnight at room temperature under vacuum.

b) Drying Dichloromethane

Dichloromethane (ANALAR from British Drug House, Poole, U.K) was dried over molecular sieve A3 (100 g per liter of solvent) overnight at room temperature.

c) Activation of PEG with Tresyl Chloride

Activation of PEG-8000 with tresyl chloride was carried out using a molar ratio of tresyl chloride to available hydroxyl groups in PEG of 2.5:1.

Dry PEG (18 g. 3.5 mmol) was dissolved in dry dichloromethane (45 mL) at room temperature. The mixture was cooled to 0° C. and stirred magnetically. Then 1.125 mL (14 mmol) pyridine (BDH, U.K.) and 1 mL (9 mmol) of tresyl chloride (Fluka AG, Switzerland) were added dropwise at 0° C. The reaction was allowed to continue at room temperature with constant stirring for 1.5 hr before the dichloromethane was removed by evaporating under reduced pressure. The remaining white solid was dried under vacuum overnight at room temperature.

d) Purification of Tresylated PEG

The crude tresylated PEG was suspended in a methanol-HCL mixture (250:1) at −20° C. for 8 hr. The solid was filtered off at 0° C., and the pyridine content in the filtrate was checked (255 nm). This procedure was repeated by using methanol-HCl (1000:1) as washing mixture until no pyridine could be detected in the filtrate. Finally, the pyridine-free tresylated PEG (12-14 g; 65-75% yield) was dried under vacuum for several hours at room temperature.

e) Reaction Between Organosilicon and Tresylated PEG

The reaction was carried out with the following steps:

(1) The organosilicon with formula

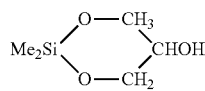

was dissolved in an aqueous phase, (2) Tresylated PEG (the amount of organosilicon is around 3% of the total weight of tresylated PEG in this example) was suspended in a sodium phosphate buffer (pH 7.5);

(3) Dispersing the sodium phosphate buffer containing said tresylated PEG into the aqueous phase, wherein the mixture was gently stirred at room temperature;

(4) Allowing the organosilicon and tresylated PEG to react at the interface of the organic phase and the aqueous phase to form a polymer-modifier complex; and (5) Separating the PEG-organosilicon complex from the solution.

Example 2: Preparation of PEG-Organosilicon Complex

Steps (a) to (d) in Example 1 were repeated.

e) Reaction Between Organosilicon and Tresylated PEG, Wherein the Organosilicon has the Formula

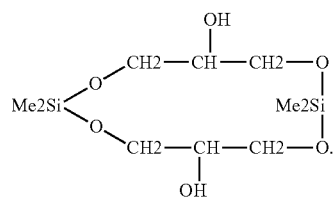

The reaction was conducted according to the following steps:

(1) Organosilicon was dissolved in aqueous phase;
(2) Tresylated PEG (the amount of organosilicon is preferably 3% of the total weight of tresylated PEG in this example) was suspended in a sodium phosphate buffer (pH 7.5); (3) Dispersing the sodium phosphate buffer containing tresylated PEG into the aqueous phase, wherein the mixture was gently stirred at room temperature;
(4) Allowing the organosilicon and tresylated PEG react at the interface of the organic phase and the aqueous phase to form a polymer-modifier complex; and
(5) Separating the PEG-organosilicon complex from the solution.

Example 3: Preparation of Target Nucleic Acids in TE Buffer

The nucleic acid-containing material was mixed with a TE buffer solution. The TE buffer comprises: 10 mM Tris (pH 8.0), 50 µM EDTA, and 20 µg/mL polyadenylic acid.

Example 4: Purification of Target Nucleic Acids by Aqueous Two Phase System with PEG-Organosilicon Complex and Salt An aqueous two-phase system was formulated in a separatory funnel through the addition of (a) 8.0 g of a 50 wt % stock solution of PEG-organosilicon complex prepared in Example 1, and (b) 10.0 g of a 15 wt % aqueous solution of potassium phosphate. One gram (1.0 g) of a solution of target nucleic acids was added into the system. The concentration of nucleic acid in the nucleic acid-containing material to be purified is 7.5 µg/mL.

The system was then diluted with distilled water to a final weight of 20.0 g, and its pH was adjusted to a pH of 4 through the addition of HCl.

The system therefore had the following composition:
20.0 wt % PEG-organosilicon complex;
7.5 wt % potassium phosphate; and
balance with water.

The system was agitated and then allowed to separate into two phases at room temperature. The phases were then isolated and the polymer phase was adjusted to a pH of 8. In one embodiment, phase separation was typically accomplished by centrifugation at 2000 rpm for 5 minutes using a refrigerated JA-14 rotor (Beckman Instruments, Fullerton, Calif.) at 4° C.

Both phases were collected for quantitative analysis of the nucleic acid after elution. The amount of the nucleic acid collected was analyzed by quantifying the wavelength absorption value of the isolated phase containing nucleic acids using a NanoDrop™ UV-Spectrophotometer at 260 nm, and the results thereof were tabulated in Table 1.

Example 5: Purification of Target Nucleic Acids by Aqueous Two Phase System with PEG-Organosilicon Complex and Salt The procedure in Example 4 was followed using the PEG-organosilicon complex prepared in Example 2. And both phases were collected for analysis. The result was summarized in Table 1. The amount of nucleic acid was quantified by the wavelength absorption using a NanoDrop™ UV-Spectrophotometer at 260 nm. The concentration fold is calculated by comparing the quantity of nucleic acid before and after purification.

Example 6: Purification of Target Nucleic Acids by Aqueous Two Phase System with PEG-Organosilicon Complex and Salt on Paper Material Porous fiberglass paper was pre-treated with the PEG-organosilicon complex prepared in Example 1, and 7.5 wt % potassium phosphate. The TE buffer containing target nucleic acids as prepared in Example 3 was poured onto the treated porous fiberglass paper, wherein the nucleic acid flowed ahead of other components. Therefore, the targeted nucleic acid was "concentrated" at the front of the fluid flow on the paper.

The amount of the biological material or nucleic acid on porous paper was collected for quantitative analysis of the nucleic acid after elution. The analysis was carried out by quantifying the wavelength absorption value of the isolated phase containing nucleic acids using a NanoDrop™ UV-Spectrophotometer at 260 nm, and the results thereof are tabulated in Table 1.

Example 7: Purification of Target Nucleic Acids by Aqueous Two Phase System with PEG-Organosilicon Complex and Salt on Paper Material The procedure in Example 6 was followed using the PEG-organosilicon complex prepared in Example 2. The result is summarized in Table 1.

Examples 8-11: Purification of Target Nucleic Acids by Aqueous Two Phase System with PEG and Salt without Modifier The procedures in Examples 4-7 were followed (Examples 8-11 respectively) using PEG instead of PEG-organosilicon. The amounts of target nucleic acids were analyzed and summarized in Table 1. The amount of nucleic acid can be quantified by the wavelength absorption using a NanoDrop™ UV-Spectrophotometer at 260 nm. Comparing the quantity before and after purification allows one to calculate the concentration fold.

TABLE 1

Amounts of nucleic acid obtained

| Example No. | Percent of nucleic acid in polymer (complex) phase (%) | Concentration fold found in polymer (complex) phase | Percent of nucleic acid in salt phase (%) | Concentration fold found in salt phase |
|---|---|---|---|---|
| 4 | 100% | 90X | 0% | — |
| 5 | 100% | 100X | 0% | — |
| 6 | 100% | 100X | 0% | — |
| 7 | 100% | 90X | 0% | — |
| 8 | 60% | 7X | 40% | 2X |
| 9 | 65% | 8X | 35% | 2X |
| 10 | 65% | 8X | 35% | 2X |
| 11 | 60% | 7X | 40% | 2X |

According to the results in Examples 4 to 11, it is clear that the binding affinity of nucleic acid for the polymer complex phase was enhanced significantly. It is surprising that 100% of the target nucleic acids can bind to the polymer complex phase once the ratio of polymer to salt is properly adjusted. In addition, the concentration of target nucleic acids was increased to an unexpected level.

The invention of using polymer-modifier complex to purify and concentrate nucleic acid in a single step is simple, easy to handle, accurate, and inexpensive, meeting the demand of commercial industry.

What is claimed is:

1. A composition for purifying and/or concentrating nucleic acids using an aqueous two phase system (ATPS), comprising:
   (i) a salt, wherein said salt is potassium phosphate;
   (ii) a polymer-modifier complex prepared by the steps of:
      (a) dispersing an organic phase comprising a modifier into an aqueous phase comprising a polymer;
      (b) allowing the polymer and modifier to react at the interface of the organic phase and aqueous phase to form said polymer-modifier complex, wherein a polymer network is formed by covalent and/or non-covalent bonds within said polymer-modifier complex; and
      (c) isolating said polymer-modifier complex in a form of suspension or solid,
   wherein said polymer is polyethylene glycol (PEG) selected from the group consisting of PEG 1000, PEG 2000, PEG 4000, PEG 8000, PEG 10000 and PEG 12000;
   said modifier is organosilicons; and
   said composition comprises 5-40% (w/w) of said polymer-modifier complex and 4-30% (w/w) of said salt;
   whereby when the composition is added to a buffer solution containing said nucleic acids to form a mixture, the mixture is separated into a polymer phase and a salt phase, wherein said nucleic acids are purified and/or concentrated in said polymer phase containing said polymer-modifier complex.

2. The composition of claim 1, wherein said organosilicons are selected from the group consisting of

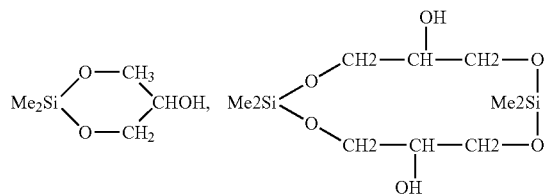

and [(CH$_3$)$_2$SiCH$_2$CH$_2$CONHCH$_2$CH$_2$Si(CH$_3$)$_2$O]$_n$ wherein n has a value of at least 2.

3. The composition of claim 1, wherein the weight ratio of the modifier to the polymer is in a range of 3% to 20%.

4. The composition of claim 1, wherein said polymer-modifier complex is suspended in water or buffer with an average particle diameter in a range of 10 nm to 500 nm.

5. The composition of claim 1, wherein said polymer-modifier complex is suspended in water or buffer with an average particle diameter in a range of 20 nm to 250 nm.

6. The composition of claim 1, wherein said composition comprises 20% (w/w) of said polymer-modifier complex and 7.5% (w/w) of said salt, wherein said polymer is PEG8000 and said organosilicons are

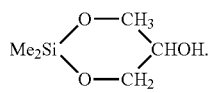

7. The composition of claim 1, wherein said composition comprises 20% (w/w) of said polymer-modifier complex and 7.5% (w/w) of said salt, wherein said polymer is PEG8000 and said organosilicons are

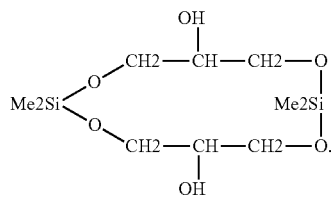

8. A method of purifying and/or concentrating nucleic acids using the composition of claim 1, said method comprising the steps of:
(1) preparing a buffer solution containing said nucleic acids;
(2) adding said composition to the buffer solution, resulting a mixture; and
(3) allowing the mixture to separate into a polymer phase and a salt phase, wherein said nucleic acids are purified and/or concentrated in said polymer phase containing said polymer-modifier complex.

9. The method of claim 8, further comprising a step of separating said nucleic acids from said polymer phase.

10. The method of claim 8, wherein said polymer network formed within said polymer-modifier complex significantly enhances the binding affinity of said nucleic acids for the polymer phase.

11. The method of claim 8, wherein 90-100% of said nucleic acids are bound to said polymer-modifier complex.

12. The method of claim 8, wherein the concentration of said purified or concentrated nucleic acids is 10-100 times higher than that of the nucleic acids in the buffer solution in step (1).

13. The method of claim 8, wherein said buffer solution is a Tris-EDTA (TE) buffer.

14. The method of claim 8, wherein said mixture comprises 5-40% (w/w) of said polymer-modifier complex.

15. The method of claim 8, wherein said mixture comprises 4-30% (w/w) of said salt.

16. A method of purifying and/or concentrating target nucleic acids using the composition of claim 1, said method comprising the steps of:
(1) Preparing said target nucleic acids in a buffer solution to form a target buffer solution;
(2) adding said composition to the target buffer solution to form a first mixture;
(3) allowing the first mixture to separate into a first polymer phase and a first salt phase, wherein said target nucleic acids predominantly partition in said first polymer phase;
(4) detecting the concentration and/or quantity of the target nucleic acids in the first polymer phase,
(5) if said concentration or quantity of said target nucleic acids from step (4) is insufficient for a subsequent analysis, mixing the first polymer phase with a new salt solution to form a second mixture, allowing the second mixture to separate into a second polymer phase and a second salt phase;
(6) repeating steps 4-5 as many times until a sufficient concentration or quantity of target nucleic acids in a final polymer phase is obtained; and
(7) isolating the final polymer phase in step (6) from the corresponding final salt phase, thereby obtaining a purified and/or concentrated target nucleic acids.

* * * * *